US008578519B2

(12) United States Patent
Kantrowitz et al.

(10) Patent No.: US 8,578,519 B2
(45) Date of Patent: Nov. 12, 2013

(54) SURGICAL GLOVE APPLIANCE DEVICE

(76) Inventors: Allen B. Kantrowitz, Miami Beach, FL (US); In Ki Mun, Nanuet, NY (US)

(*) Notice: Subject to any disclaimer, the term of this patent is extended or adjusted under 35 U.S.C. 154(b) by 44 days.

(21) Appl. No.: 12/959,782

(22) Filed: Dec. 3, 2010

(65) Prior Publication Data

US 2012/0137402 A1 Jun. 7, 2012

(51) Int. Cl.
*A41D 19/00* (2006.01)

(52) U.S. Cl.
USPC ............................. 2/161.7; 2/168; 223/111

(58) Field of Classification Search
USPC ................. 2/16, 162, 163, 161.1, 161.7, 168; 223/111
See application file for complete search history.

(56) References Cited

U.S. PATENT DOCUMENTS

| | | | | | |
|---|---|---|---|---|---|
| 312,518 | A | * | 2/1885 | Sohoenoff | 2/216 |
| 2,169,939 | A | * | 8/1939 | Anderson | 441/57 |
| 2,266,716 | A | * | 12/1941 | Robertson | 2/168 |
| 2,299,855 | A | * | 10/1942 | Sterling | 2/168 |
| 2,641,767 | A | * | 6/1953 | La Rosa | 2/168 |
| 2,707,283 | A | * | 5/1955 | Silver et al. | 2/159 |
| 3,099,015 | A | * | 7/1963 | Renehan | 285/260 |
| 3,231,910 | A | * | 2/1966 | Tegland | 441/57 |
| 3,235,881 | A | * | 2/1966 | Chisholm | 2/167 |
| 3,283,338 | A | * | 11/1966 | Landau | 2/161.6 |
| 3,386,104 | A | * | 6/1968 | Casey | 2/16 |
| 3,476,109 | A | * | 11/1969 | Hurney | 602/1 |
| 3,602,917 | A | * | 9/1971 | Seunevel et al. | 2/167 |
| 3,811,132 | A | * | 5/1974 | Segonzac et al. | 2/270 |
| 4,069,913 | A | * | 1/1978 | Harrigan | 206/278 |
| 4,141,609 | A | * | 2/1979 | Eisert | 312/1 |
| 4,275,812 | A | * | 6/1981 | Poncy et al. | 206/278 |
| 5,093,933 | A | * | 3/1992 | Berry | 2/161.6 |
| 5,380,078 | A | * | 1/1995 | Baczkowski et al. | 312/1 |
| 5,816,440 | A | | 10/1998 | Shields et al. | |
| 5,921,434 | A | | 7/1999 | Hollander et al. | |
| 5,975,083 | A | | 11/1999 | Henderson, Jr. | |
| 6,193,117 | B1 | * | 2/2001 | Poschelk | 223/111 |
| 6,375,034 | B1 | | 4/2002 | Corbett | |
| 6,839,912 | B2 | * | 1/2005 | Lewis | 2/161.6 |
| 7,063,233 | B2 | | 6/2006 | Jordan et al. | |
| 7,527,181 | B1 | * | 5/2009 | Sullivan | 223/111 |
| 2002/0040912 | A1 | | 4/2002 | McHugh | |
| 2004/0172918 | A1 | * | 9/2004 | Jordan et al. | 53/429 |
| 2005/0015847 | A1 | | 1/2005 | Scheele et al. | |
| 2006/0107437 | A1 | * | 5/2006 | Griesbach | 2/114 |
| 2007/0118964 | A1 | | 5/2007 | Sacco et al. | |
| 2007/0120682 | A1 | * | 5/2007 | Rea et al. | 340/572.8 |
| 2007/0284387 | A1 | | 12/2007 | Ellswood et al. | |
| 2008/0011766 | A1 | | 1/2008 | Jordan et al. | |

* cited by examiner

*Primary Examiner* — Richale Quinn
(74) *Attorney, Agent, or Firm* — Blue Filament Law PLLC; Avery N. Goldstein

(57) ABSTRACT

A protective barrier, such as a medical examination glove is provided that includes a bracelet defining a plane with a cylinder attached to the bracelet at a first end. The cylinder is compressed into a compressed conformation in the plane without rolling about the bracelet. When the barrier is a glove, three fenestrated caps are provided, each such cap attached to the cylinder at different locations along the length of the cylinder when said first cylinder is in an extended conformation. Multiple finger cylinders are each attached to the cylinder at a location of a fenestrated cap, the finger cylinders each having an end cap. The first cylinder and the finger cylinders each compressed into a compressed conformation in the plane such that each of the caps forms a portion of the surface of the plane.

9 Claims, 2 Drawing Sheets

SURGICAL GLOVE APPLIANCE DEVICE

FIELD OF THE INVENTION

The invention relates to easy to use and comfortable sanitary barriers used for medical examination or applying protective material to areas of the body such as the fingers, hands, or feet.

BACKGROUND OF THE INVENTION

The medical field is continually frustrated by hospital-borne infections that may be due in part to lack of regular use of barrier protection between a care provider and a patient. Care providers make every attempt to regularly use medical examination gloves when interacting with patients, but due to difficulty of their use or discomfort in their fit, donning examination gloves is too often overlooked. Typical examination gloves are made of materials that are intended to fit tightly around the fingers, palm, and wrist of a subject so as to promote maximum freedom of movement and feel transmission through the glove material. This tight fit, however, also increases the difficulty of inserting a hand into the glove. Examination gloves commonly tear or are otherwise compromised while a user is inserting his hand into the glove simply due to the tight fit of the glove. This risk of tearing is even more prevalent when the glove is made of materials such as nitrile that historically do not have the same elasticity of natural latex.

Tight fitting examination gloves also lead to perspiration under the glove due to lack of ventilation. This perspiration can produce a slippery connection to the hand that may cause the glove to fold over on itself further decreasing the user's comfort.

To reduce perspiration or increase comfort, some individuals use gloves that are sized for a larger person. The larger gloves, however, are proportioned to have longer finger regions with increased diameter. A user is, thus, left with a loose-fitting glove at the fingers that makes handling small equipment difficult and otherwise reduces dexterity.

Another problem with current examination gloves is that they are packaged into a container in such a manner that their removal is sometimes difficult without also tearing the glove or otherwise compromising the glove's sterility. Of greatest concern to hospitalized patients who are immunocompromised or otherwise susceptible to infection is that gloves of the prior art require a user or assistant to grasp the outside of the glove during removal from a dispenser or insertion of a hand which commonly leads to contamination and increased risk of transmission of infectious agents to the patient. This risk is much higher in non-surgical situations where assistance from another person in donning sterile gloves is not available.

All of these problems of currently used examination gloves reduce the compliance of healthcare professionals in wearing protective barrier equipment when handling or interacting with patients. As such, there is a need for an improved barrier protection that will increase user compliance and simultaneously decrease the risk or prevalence of transmission of infectious agents from a healthcare worker to a patient or vice versa.

SUMMARY OF THE INVENTION

A barrier for protecting a user is provided that includes a bracelet connected to a cylinder at a first end where the cylinder is compressed into a plane of the bracelet prior to deployment. The first cylinder is compressed by rolling such as by a midpoint roll, folding such as by an accordion fold, or other, but is not rolled about the bracelet. In some embodiments a cylinder is made of a biofluid-impermeable material.

A barrier optionally includes a plurality of cylinders including a first cylinder attached to one or more finger cylinders to form the conformation of a glove. When each of the cylinders is compressed into the plane of the bracelet, the barrier is readily deployable. A first cylinder optionally includes one or more ribs that may be more rigid than the cylinder wall itself. One or more bands that contract the cross-sectional area of a cylinder are optionally included. Such bands optionally serve to assist retaining the barrier on a user. A barrier optionally includes one or more end caps attached to a distal end of a cylinder or continuous therewith. An end cap is optionally made from material of increased pliability relative to the wall of a cylinder and may form a conformational fit over an object inserted therein. A marking is optionally included on an end cap or other portion of a cylinder.

A bracelet optionally includes one or more communications devices that may be active or passive. In some embodiments a communications device is optical, radiofrequency, or other.

A medical examination glove is also provided that includes a bracelet defining a plane, a first cylinder attached to the bracelet at a first end, and one or more fenestrated caps defining the regions where a plurality of finger cylinders are attached to the first cylinder. The finger cylinders each include an end cap. Each finger cylinder and the first cylinder are compressed into a plane defined by the bracelet. The glove is optionally compressed by a midpoint roll and an accordion fold in a first cylinder and a midpoint roll in each of the finger cylinders. A rib is optionally included within a wall of the first cylinder where the rib is more rigid than the wall of the cylinder. At least one band is optionally provided that contracts the cross-sectional area of the cylinder in the area of the band. A bracelet optionally includes one or more communications devices such as an RFID tag.

A system of monitoring use of a barrier in a site is also provided wherein use of a barrier or medical glove is recorded following a scanning device receiving a signal from the communications device.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention, but are presented for illustrative and descriptive purposes only.

Figure 1:
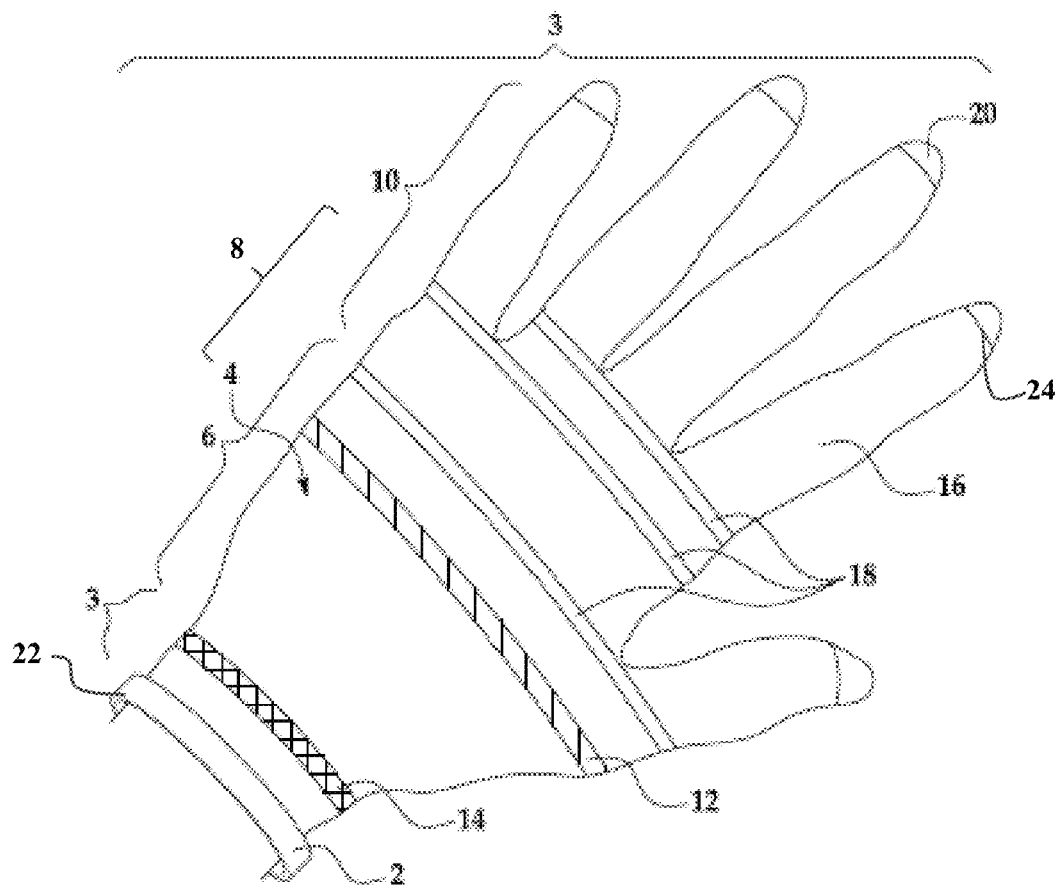
FIG. 1 illustrates one embodiment of a barrier.

A barrier is provided illustratively in the form of a glove or a shoe cover that has utility in protecting healthcare workers or others from infectious agents and improving healthcare worker compliance in the wearing of protective equipment. One embodiment of the invention can be understood by reference to FIG. 1. FIG. 1 is a perspective view of a barrier in the conformation of a medical examination glove that is formed of a plurality of cylinders affixed to a bracelet. A barrier 1 includes a bracelet 2 defining a plane that is attached to a first cylinder 4 at a first end of the first cylinder 4. A bracelet 2 has a width, cross-sectional length, and cross-sectional area. A plane defined by a bracelet 2 is appreciated to be of width optionally substantially equal to or smaller than the width of the bracelet 2 and is at most no wider than a cross-sectional area of the bracelet. As such, when a cylinder is compressed into a compressed conformation the entire cylinder can be within the plane. A bracelet 2 is optionally continuous or discontinuous in outer circumference. In some embodiments a bracelet 2 is discontinuous in outer circumference such that it is collapsible for storage or transport yet may be opened to accept an object in the interior of the bracelet 2. It is appreciated that a bracelet 2 optionally includes a fastener openable to sufficient dimension that a human hand or foot, optionally that of an adult, can fit through the center portion of the bracelet 2 and allow the hand or foot to contact a portion of a cylinder. A bracelet 2 can be made of any material with suitable rigidity to either hold a shape on its own or with additional support. Illustratively, a bracelet is made of any polymeric material such as thermoplastics or thermoset resins. Other illustrative materials include metals such as stainless steel, glass, natural or synthetic rubbers such as latex rubber, nitrile, vinyl, or other materials known in the art.

A length reducing first cylinder 4 is attached to a bracelet 2 at a first end. A cylinder 4 is optionally made of the same or a different material than that of the bracelet 2. In some embodiments a first cylinder is made of a biofluid-impermeable material that is either of synthetic or natural origin. Illustrative examples include latex, vinyls, or nitriles. In some embodiments, the material of a first cylinder is not biofluid impermeable yet will be sufficient to offer sanitary protection to a user. Illustrative examples include flexible vinyl or plastic sheeting or other materials known in the art.

A first cylinder 4 optionally includes three regions. A wrist region 6 is appreciated as being proximal to a bracelet 2 and interconnected therewith. This wrist region 6 is continuous with a palm region 8 that may be of greater or similar cross-sectional area as that of the wrist region. The palm region 8 is optionally interconnected to a finger region 10. A wrist region, palm region, or both optionally have greater cross-sectional area than a bracelet. A finger region 10 optionally includes one or more finger cylinders 16 attached to a region of a first cylinder 4 at a point distant from the first end such as in the area of a palm region 8. In some embodiments, the finger cylinders 16 are of smaller cross-sectional area than a first cylinder and can be independently tailored to a user's finger size.

A terminal end of one or more finger cylinders is optionally dimensioned so as to form conformational contact with a phalanx of a subject. The human fingers typically have a diameter of 12 to 23 millimeters and a circumference of 40 to 70 millimeters. As such a dimension of at least a portion of a finger cylinder, such as any cross-sectional length, is smaller or within the range of typical human finger diameter. The cross-sectional area of a finger cylinder 16, or a first cylinder 4, is optionally uniform or variable. It is appreciated that a terminal end 20 of a finger cylinder 16 is optionally of smaller cross-sectional area than an insertion end so that a subject's finger upon insertion into a finger cylinder 16 allows conformational contact to occur at the fingertip while a looser fit is achieved at the base of the finger.

A first cylinder 4 optionally includes one or more fenestrated caps 18 that represent a division between a first cylinder 4 and one or more finger cylinders 16. As illustrated in FIG. 1, five finger cylinders 16 are connected to a single first cylinder 4 via a plurality of fenestrated caps 18. A first fenestrated cap is positioned at a location in a first cylinder 4 to define the base of a first finger cylinder that is optionally intended to accept the thumb of a subject. An optional second fenestrated cap 18 defines the intersection between a first cylinder 4 and a finger cylinder 16 that is optionally intended to accept a digitus minimus of a subject's hand. Also due to the traditional anatomical structure of a hand, a third fenestrated cap 18 is optionally located further terminal on a first cylinder 4 to define an intersecting region between the first cylinder 4 and as many as three additional finger cylinders 16 that are optionally designed to accept a digitus secundus manus, a digitus medias, or a digitus annularis. In some embodiments, a fenestrated cap is merely a region demarking the beginning of any other cylinder attached to a first cylinder. The one or more fenestrated caps 20 are optionally made from the same or different material as a first cylinder or a finger cylinder. A fenestrated cap 20 is optionally of greater or reduced elasticity from the first cylinder wall material or the material of a finger cylinder. Decreased elasticity is optionally achieved by a thickening in the material that defines the location of the fenestrated cap. This thickening in the material at these locations optionally serves to increase the resilience of the material and decrease the likelihood of tears at these locations.

A first cylinder 4 and/or one or more finger cylinders 16 optionally includes an end cap 20 that closes an end of the cylinder. An end cap 20 provides a closed terminal end to the cylinder, thus, creating barrier protection around the entire cylinder 4 excepting the bracelet 2. An end cap 20 is optionally attached to or continuous with the wall of a cylinder. An end cap 20 is optionally continuous with the wall of an adjacent cylinder. An end cap 20 is optionally made of similar material or different material than the cylinder 16 to which it is attached. In some embodiments, the area of the end cap 20 is made of a material with decreased thickness or increased elasticity relative to the cylinder to provide improved conformational fit around the distal portion of a user's finger.

A first cylinder 4 or a finger cylinder 16 optionally includes one or more ribs 12 that may be made of stiffer material or a thicker material than that which comprises the cylinder. A rib 12 is optionally included within the wall structure of a cylinder and prevents the lumen of the cylinder from collapsing after deployment. It is appreciated that several ribs may be included at different locations within the same or different cylinders 16 on a barrier. A first rib 12 is optionally located in the palm region which helps maintain a loose fit over the palm of a user thereby increasing comfort and decreasing the likelihood of excessive perspiration. Additional ribs are optionally located at the base of each finger cylinder 16 near the fenestrated cap 20 or near the joints between the proximal and intermediate phalanges of a user. Inclusion of one or more ribs also increases user comfort and flexibility while still allowing conformational contact around the distal phalanx of a subject.

One or more bands 14 are optionally included at one or more regions within a barrier. Bands are localized segments of elastic material that are also optionally included within the wall structure of a cylinder 4 which encourages the lumen of the cylinder to reduce in cross-sectional area after deployment to help the cylinder 4 conform closely to the shape that is contained therein at the point of the band 14. In one embodiment, a band 14 is located in the wrist region 6 that, after deployment, helps secure the barrier to the hand of a user while still allowing a loose fit in the palm region. A band 14 is optionally made out of the same material or different material as that of the cylinder into which it is incorporated. A band 14 is optionally an area of increased thickness or simply reduced cross-sectional area.

In some embodiments, when a user inserts a hand into a bracelet, the ends of the fingers come into conformational contact with the material of the first cylinder 4, one or more finger cylinders 16, or end caps 20 thereon. It is appreciated that this conformational contact need extend only around the fingertips of the subject thus maintaining a user's dexterity and feel illustratively for handling small objects or examining a patient. Other than the conformational contact around the fingertips 20, it is appreciated that a cylinder 4 is optionally sufficiently dimensioned to fit relatively loosely around a user's palm and/or wrist. Relatively loosely is meant to refer to a loose fit relative to that of a traditional prior art latex or nitrile glove that is commonly used for medical examination. The conformational contact at the fingertips combined with the relatively loose fit around the palm and/or wrist of a subject leads to increased comfort and corresponding increased user compliance.

Prior to being deployed, a cylinder 4 is optionally rolled or folded into a planar shape within the cross-sectional area of a bracelet 2. It is appreciated that different cylinders or different regions of the same cylinder are compressed, folded, or rolled so as to create an overall planar shape of the entire barrier structure optionally within the internal dimension of the bracelet.

An inventive cylinder optionally includes a marking 24. A marking 24 optionally illustrates the location to place a finger or a portion of the foot into a region within the cross-sectional area of a bracelet to allow for maximal ease of deployment of the barrier. In some embodiments five markings are included at each of the end caps 20 on finger cylinders 16. Markings 24 are optionally a different color, texture, material, or other discernable difference, than the remainder of the barrier so a user can readily see where to stick the distal portion of each phalanx to direct him to the conformational contact portion of each of the finger cylinders thereby maximizing ease of deploying the barrier and without the need for sliding the barrier material over any portion of the hand. Prior art barrier deployment typically requires a user to slide his or her hand across the barrier material to find an end where a fingertip is to be located. A barrier as provided by the subject invention optionally eliminates sliding an object into a cylinder by using a folding and/or rolling mechanism that allows the terminal region or end cap to be immediately contacted by a subject's finger as a first point of insertion. This creates maximal conformational contact between the fingertip and the end cap and easy and rapid deployment of the remainder of the barrier over the subject's hand.

In some embodiments, a bracelet 2 includes a communications device 22. A communications device is optionally referred herein as a tag. Illustrative examples of tags such as identification tags operable as a communications device are found in U.S. Publication No. 2005/0258939, the contents of which are incorporated herein by reference. A communications device 22 is optionally configured to receive, store, transmit, or combinations thereof, data such as data indicating usage of a barrier, time of use, moving a bracelet into a site, or other information.

A communications device 22 is optionally coupled to a scanning device such that transmitting energy or signals between a communications device and a scanning device or vice versa allows the transfer of information to or from a communications device. An illustrative example of a communications device 22 is a radiofrequency identification (RFID) tag. With the emergence of an RFID standards authority, a tag is readily tracked to a specific source such as a particular barrier. Owing to the data-carrying capacity of a tag, a large number of tags are capable of rapid interrogation. The size of a tag is optionally on the scale of 1 to 500 microns allowing ready labeling of a bracelet or other region of a barrier.

A communications device 22 is optionally located on a bracelet surface or is embedded in the structural material of the bracelet. Use of an RFID tag optionally creates an active bracelet capable of communicating information to a scanning device and thereby facilitating information exchange with a computer database. An RFID tag is optionally active or passive. Active and passive RFID tags, their manufacture, and use are known in the art. In some embodiments a passive RFID tag is used where a scanning device emits a radiofrequency signal that energizes a coiled antenna from which the tag draws power, thus, emitting a signal that is receivable by the scanner or other receiving device. Such devices are illustratively described in U.S. Pat. No. 5,053,774, the contents of which are incorporated herein by reference. Optionally, a communications device uses "smart card" technology, the resulting barrier operating in a manner as is apparent to one skilled in the art. A communications device 22 optionally communicates identifying information alone or is additionally or alternatively capable of reporting more complex information such as environmental measurements and other information such as is described in U.S. Pat. Nos. 5,287,113; 5,532,686; 5,257,011; 6,078,251; and 6,617,963, the contents of each of which are incorporated herein by reference.

In some embodiments, a communications device 22 functions to passively communicate information such as use or identification information to a scanning device. Optionally, a monochromatic optical signal emitted by a scanning device is directed to a passive tag. The optical signal optionally has a wavelength ranging from ultraviolet through visible to infrared. Optical signals are optionally monochromatic and emitted by a scanning device that includes a laser or photodiode, or the signal is polychromatic optionally such as that obtained from an incandescent light source. A passive communications device optionally includes a reflective or retro-reflective transponder that interacts with the incoming optical signal to return a reflected output signal communicating an identification code. The identification tag may communicate information specific to the barrier, the barrier type, lot, origin of manufacture, or may simply identify that a barrier is used within a site. Methods of encoding a tag with a unique code illustratively include the deposition of bandpass filter coatings onto a reflective surface of the passive optical identification tag; the placement of one or more dye molecules onto the surface, the dye molecules being stimulated by the incoming optical signal so as to emit a characteristic reflection wavelength, fluorescence, or phosphorescence; and scoring a reflective surface to create light scattering of an incoming optical signal of a predetermined magnitude.

In particular embodiments, an inventive barrier is a foot cover. A foot cover is optionally a sterile cover such as that used in surgical areas, or a sterile or non-sterile cover the like of which is useful at security sites. A bracelet is attached to a first cylinder that is made of protective, but not necessarily biofluid-impermeable material, and may but need not be sterile. The first cylinder includes an end cap that is attached to or continuous with the wall of the cylinder. When a user places a foot into the plane of the bracelet, the barrier contacts the initially entering foot portion and deploys along the length of the foot. A foot is thereby enveloped by the first cylinder. A cylinder and bracelet are optionally suitably dimensioned to accept a foot, or portion thereof, and deploy around the inserted foot area.

It is appreciated that a barrier is optionally provided in pairs. In embodiments where a barrier is a glove, a barrier is optionally tailored to fit the right hand or left hand of a user. Thus, barriers are optionally provided in right and left pairs. In other embodiments, a barrier may be provided in pairs, but each barrier is indistinguishable from the other. Illustratively, a barrier is intended to accept a foot of a user. Due to the generally loose fit of the barrier, there may be no need to provide a right or left hand specific barrier in a pair.

Also provided with an inventive barrier is a system that can be used to monitor compliance of barrier use within a specific site such as a curtain perimeter. In some embodiments, a barrier is provided with a communications device located on the barrier wall, on the bracelet, or both. A "site" is defined by some geographical characteristics, coordinates like longitude and latitude obtained from a GPS-type reading, or a geographic or physical location associated with a scan event by a particular scanning device. In some embodiments a site is a patient's room or treatment area. When a barrier is deployed within a site, a signal is readable by a scanning device and communicated to a database to record the use of the barrier within the site area.

A scanning device is used at a site to interrogate the site for the presence of a deployed barrier and communicate the use of a barrier to a database which records such use. The database includes application-specific information that illustratively includes compliance information, administration information, inventory information, treatment information, or combinations thereof. Based on the recording of information and comparison with treatment delivery, user compliance is readily measured. A database also records usage information so as to provide a measure of inventory levels and alert an operator that more barriers are needed in a particular site.

A scanning device optionally is used to monitor a site for the presence of a deployed barrier. A scanning device optionally emits a signal such as an infrared signal, radiofrequency signal, ultrasonic signal, or other signal that is receivable, reflectable, or other, by a tag on a barrier. In some embodiments in which an active communications device is used, a scanning device is in a receive mode so that a signal emitted by a communications device is read by the scanning device when a barrier is used in a site area. Upon receiving a signal from a communications device, that the device is deployed within the site, such use is communicated to a database that is housed within the communications device or is remote therefrom such as hosted by a remote computer system in communication with the scanning device. The barrier type, source, specific identifier, or other barrier information is recorded in the database. A database optionally stores the identification of a user. A user optionally scans illustratively an identification badge prior to entering a site. When the user deploys a barrier the use of the barrier is correlated with the user within the site. This allows monitoring and metrics of user compliance and identification of users that require remediation.

In one embodiment, a passive tag is located on a bracelet or the wall of a barrier. A site is a treatment area monitored by one or a plurality of scanning devices defining the dimensions of the site. When a barrier is removed from a dispenser that shields the tag from the scanners, the passive tag is then operable to communicate a signal to a scanning device that the barrier has been removed from the dispenser and is therefore deployed by the user. The scanner communicates the received signal to a database that records the barrier use. An illustrative example of a passive tag is described in U.S. Publication No. 2005/0258939, the contents of which are incorporated herein by reference.

In some embodiments a communications device is printed or otherwise located directly on the surface of a cylinder. Illustratively, an optical tag is located on a cylinder that when the cylinder is deployed such as by unrolling, unfolding, or combinations thereof, the optical tag is then positioned to communicate a signal to a scanning device. This prevents recording use of a barrier absent its actual deployment.

In some embodiments the communications device is used to create an audit trail of patient contact. Each time a user deploys a barrier its use is recorded as an event of patient contact. The event can be correlated with a treatment type, time, location of the site, patient identification, or identification of the user to create a recorded trail of patient contact. This information can be used to confirm that a particular user interacted with a patient, that a barrier was used in a site area, or that a particular treatment was properly delivered.

Communications devices on a foot barrier, a hand barrier, or any other barrier type, optionally emit, reflect, or redirect distinguishable signals so that use of illustratively a glove barrier, a foot barrier, or both are simultaneously or sequentially detected by a scanning device and their deployment recorded in a database.

Figure 2A:
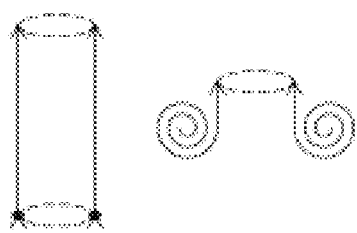
FIG. 2 illustrates alternate methods of compressing a barrier or portion thereof including an endpoint roll (A) or a midpoint roll (B)
Figure 2B:
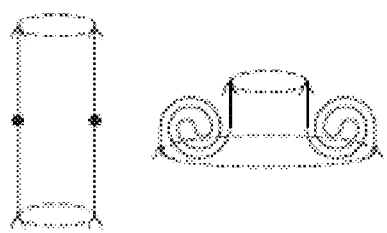

FIG. 2 illustrates two optional methods of rolling a cylinder. FIG. 2A illustrates an endpoint roll where one terminal end of a cylinder serves as the initiation point of the roll. The cylinder lumen is rolled around this initiation point until the terminal end or the end that includes a simple cap is in a relative planar orientation to the initiation point of the roll. FIG. 2B illustrates a midpoint roll where a roll is initiated at some point between a proximal end and distal end of a cylinder. A proximal end is defined herein as the end nearest a bracelet. A midpoint roll offers the advantage of allowing several cylinders that are attached to each other, such as a first cylinder which is attached to a finger cylinder, to be independently rolled to form an overall planar shape and increase ease of deployment by allowing simultaneous or sequential unrolling of each of the cylinders in independent fashion. It is appreciated that any point between the proximal and distal ends of a cylinder can serve as the initiation point of a midpoint roll. In some embodiments, the initiation point of the midpoint roll is near the midpoint of the cylinder length.

Figure 3A:
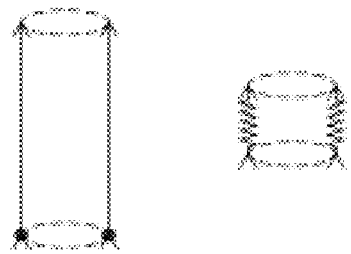
FIG. 3 illustrates alternate methods of compressing a barrier or portion thereof including an accordion fold (A) or a bellows fold (B)
Figure 3B:
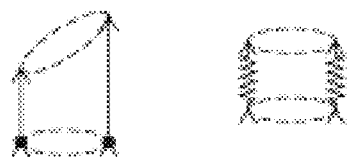

Other methods of forming a planar shape from one or more cylinders illustratively include folding schemes such as those depicted in FIG. 3. FIG. 3A illustrates an accordion fold which in the case of a cylinder is a circular fold that results in a fan-like compression of the cylinder lumen. Another illustrative fold is depicted in FIG. 3B as a bellows fold. A bellows fold serves to longitudinally collapse a cylinder that may have nonparallel ends or other non uniform shape. U.S. Pat. No. 6,054,194 illustrates many different mechanisms for bellows folding and is incorporated herein by reference.

Figure 4A:
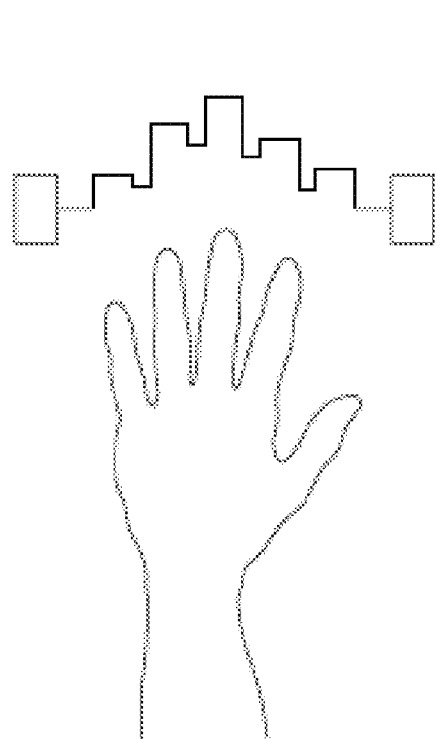
FIG. 4 illustrates one embodiment of a compressed barrier of FIG. 1 (A) and its subsequent deployment by insertion of a user's hand (B).
Figure 4B:
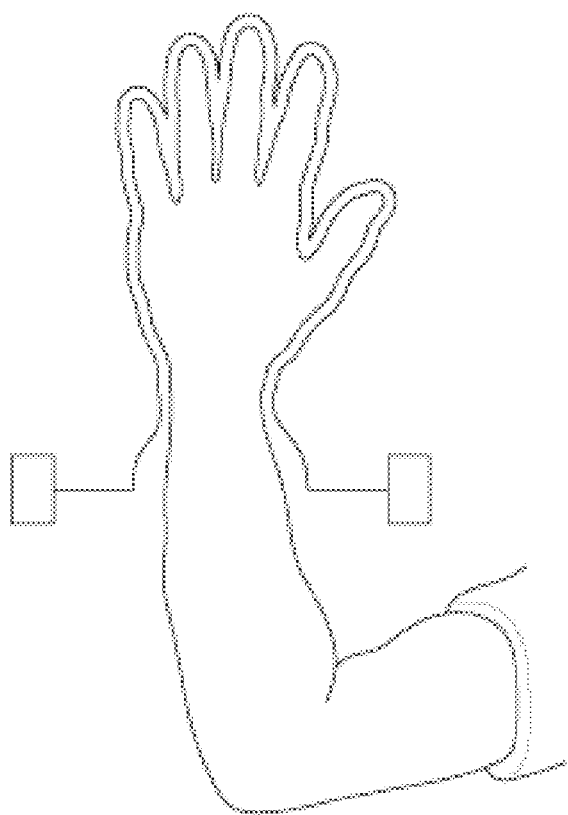

An overall planar shape of one or more cylinders is optionally achieved by various combinations of folds or rolls at different locations within the wall of a single cylinder or a plurality of cylinders depending on the barrier type that is used. FIG. 4A illustrates one embodiment of a barrier in the form of a glove that is folded and rolled at various locations on a plurality of cylinders so as to form an essentially planar shape within the plane of the bracelet. FIG. 4A illustrates a compressed form of the barrier of FIG. 1. A first cylinder is compressed by a midpoint roll up to the point of a first fenestrated cap. This first fenestrated cap illustrates the division between a first cylinder and a finger cylinder that is operable to accept a thumb. The finger cylinder operable to accept a thumb is rolled via a midpoint roll into essentially the same plane as that of the lower portion of the first cylinder. Above or distal to the first fenestrated cap, the first cylinder is optionally folded by an accordion fold up to a second fenestrated cap that serves as a division between a first cylinder and a finger cylinder operable to accept a digitus minimus. This digitus minimus finger cylinder is optionally rolled via a midpoint roll also into the same plane as the first cylinder. A second accordion fold is optionally included between the second fenestrated cap and the third fenestrated cap. Above an optional third fenestrated cap, three finger cylinders are attached to the first cylinder, each finger cylinder is rolled by a midpoint roll. This overall configuration collapses a barrier in the form of a glove into an essentially single plane. Collapsing a barrier in this or other manner exposes the end caps as sides of the established plane and able to accept initial contact of a hand upon insertion into the bracelet. Collapsing the cylinders into the plane also allows rapid and easy insertion of a subject's finger or entire hand (see FIG. 4B) into a barrier for rapid deployment without the risk of contaminating the external surface of the barrier, increased likelihood of tearing the barrier, or other compromise. By exposing the end caps to the plane of the compressed barrier, a user merely deploys the barrier by moving his hand through the bracelet whereby the barrier deploys around the hand minimizing any required sliding. It is appreciated that other compression mechanisms such as different combinations of rolls and folds are equally applicable, envisioned by one of ordinary skill in the art in view of the specification, and within the scope of the present invention.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A pre-folded protective barrier for a hand comprising:
a bracelet defining a plane;
a first cylinder made of at least one of latex or nitriles having a first end, said first cylinder attached to said bracelet at said first end and said first cylinder compressed into a compressed conformation in said plane without rolling about said bracelet; and
wherein said pre-folded barrier has said first cylinder compressed by a midpoint roll up to a point of a first fenestrated cap serving as a division between said first cylinder and a first finger cylinder that is operable to accept a thumb, said first finger cylinder rolled via a midpoint roll into the same plane as that of a lower portion of said first cylinder, and wherein above or distal to said first fenestrated cap, said first cylinder is folded by a first accordion fold up to a second fenestrated cap that serves as a division between said first cylinder and a second finger cylinder operable to accept a digitus minimus, said second finger cylinder is rolled via a midpoint roll into the same plane as said first cylinder, and a second accordion fold is included between the second fenestrated cap and a third fenestrated cap, wherein above said third fenestrated cap, three finger cylinders are attached to said first cylinder, each of said three finger cylinders being rolled by a midpoint roll, such that a length of s id pre-folded protective barrier is reduced for easy insertion of said hand.

2. The barrier of claim 1 wherein said first cylinder comprises a biofluid impermeable material.

3. The barrier of claim 1 wherein said first cylinder further comprises a wrist region, and a palm region wherein said wrist region, said palm region, or both have a greater cross sectional area than said bracelet.

4. The barrier of claim 1 wherein said first cylinder further comprises at least one rib within a wall of said first cylinder wherein said rib is more rigid than a wall of said first cylinder.

5. The barrier of claim 1 wherein said first cylinder comprises at least one band that contracts a cross sectional area of said cylinder in the area of said band.

6. The barrier of claim 1 wherein said first finger cylinder, said second finger cylinder, and said three finger cylinders further comprise an end cap wherein said end cap closes an end of each of said cylinders.

7. The barrier of claim 6 further comprising a marking at the position of an end cap.

8. The barrier of claim 1 wherein said bracelet or said material further includes a communication device.

9. The barrier of claim 8 wherein said communication device is an RFID tag.

* * * * *